United States Patent
Dunaway et al.

(10) Patent No.: US 12,306,165 B2
(45) Date of Patent: May 20, 2025

(54) PROBE SYSTEM WITH DETACHABLE SENSOR PROBE THAT COMMUNICATES WIRELESSLY

(71) Applicant: HACH COMPANY, Loveland, CO (US)

(72) Inventors: Scott S. Dunaway, Loveland, CO (US); David E. Lotton, Erie, CO (US)

(73) Assignee: HACH COMPANY, Loveland, CO (US)

( * ) Notice: Subject to any disclaimer, the term of this patent is extended or adjusted under 35 U.S.C. 154(b) by 391 days.

(21) Appl. No.: 17/687,999

(22) Filed: Mar. 7, 2022

(65) Prior Publication Data
US 2023/0280325 A1   Sep. 7, 2023

(51) Int. Cl.
G01N 33/18 (2006.01)
G01N 33/00 (2006.01)
H02J 50/10 (2016.01)
H04B 1/40 (2015.01)

(52) U.S. Cl.
CPC ......... *G01N 33/18* (2013.01); *G01N 33/0075* (2013.01); *G01N 33/1886* (2013.01); *H02J 50/10* (2016.02); *H04B 1/40* (2013.01)

(58) Field of Classification Search
CPC ............... G01N 33/18; G01N 33/1886; G01N 33/0075; H02J 50/10; H04B 1/40
See application file for complete search history.

(56) References Cited

U.S. PATENT DOCUMENTS

| | | | |
|---|---|---|---|
| 9,660,325 B2 | 5/2017 | Haase et al. | |
| 9,671,339 B2 | 6/2017 | Haase et al. | |
| 9,762,290 B2 | 9/2017 | Pilz | |
| 2002/0038392 A1* | 3/2002 | De La Huerga | G16H 20/17 710/8 |
| 2002/0193910 A1* | 12/2002 | Strege | G05B 23/0221 700/279 |
| 2007/0208841 A1* | 9/2007 | Barone | B61L 15/0027 709/223 |
| 2008/0184827 A1* | 8/2008 | Susfalk | G01D 9/005 73/866.5 |
| 2011/0004186 A1* | 1/2011 | Butterfield | G16H 10/40 340/603 |

(Continued)

FOREIGN PATENT DOCUMENTS

| | | |
|---|---|---|
| EP | 2 883 445 B1 | 1/2018 |
| WO | 2020/148486 A1 | 7/2020 |

OTHER PUBLICATIONS

Apr. 25, 2023 International Search Report and Written Opinion of the International Patent Application No. PCT/US23/10914.

*Primary Examiner* — Helen C Kwok
(74) *Attorney, Agent, or Firm* — Oliff PLC

(57) ABSTRACT

A probe is described that is configured to measure a parameter of a liquid, such as water. The probe includes a probe head and a sensor probe that is detachably coupled to the probe head. The probe head and the sensor probe each include a radio frequency (RF) transceiver. The sensor probe measures the parameter of the liquid and transmits data relating to the measured parameter to the probe head by the RF transceivers. The probe can optionally include an inductive power coupling between the probe head and the sensor probe, and an interface between the probe head and sensor probe can be free of conductive connections.

18 Claims, 6 Drawing Sheets

(56) References Cited

U.S. PATENT DOCUMENTS

| | | | |
|---|---|---|---|
| 2011/0273165 A1* | 11/2011 | Palassis | G01D 11/00 |
| | | | 324/149 |
| 2014/0130621 A1 | 5/2014 | Palassis et al. | |
| 2014/0167519 A1 | 6/2014 | Pilz | |
| 2015/0007636 A1 | 1/2015 | Benkert et al. | |
| 2015/0148983 A1* | 5/2015 | Fitzgibbon | G05B 19/41855 |
| | | | 700/302 |
| 2015/0155892 A1 | 6/2015 | Haase et al. | |
| 2015/0195011 A1 | 7/2015 | Birgel et al. | |
| 2015/0293877 A1 | 10/2015 | Liang et al. | |
| 2015/0333534 A1* | 11/2015 | Liu | H02J 5/00 |
| | | | 307/104 |
| 2016/0161405 A1 | 6/2016 | Haase et al. | |
| 2016/0183484 A1* | 6/2016 | Richings, Sr. | A01G 25/167 |
| | | | 239/11 |
| 2017/0359674 A1* | 12/2017 | Nair | H04W 4/021 |
| 2018/0085605 A1* | 3/2018 | Maharbiz | A61B 5/279 |
| 2018/0096576 A1* | 4/2018 | Anderholm | G01S 13/886 |
| 2018/0136354 A1 | 5/2018 | Haldorsen | |
| 2019/0226886 A1* | 7/2019 | Bromley | G01L 5/243 |
| 2019/0243015 A1 | 8/2019 | Adams et al. | |
| 2019/0339133 A1* | 11/2019 | Pulvermacher | G01K 1/022 |
| 2020/0303950 A1* | 9/2020 | Roberts | G08B 21/185 |
| 2020/0383614 A1* | 12/2020 | Bechtel | A61B 1/00181 |
| 2020/0393333 A1 | 12/2020 | Cheng | |

\* cited by examiner

PROBE SYSTEM WITH DETACHABLE SENSOR PROBE THAT COMMUNICATES WIRELESSLY

BACKGROUND

To evaluate the quality of water and other liquids, parameters of the liquid such as pH, dissolved oxygen, conductivity, and oxidation reduction potential (ORP) can be measured and monitored. Sensor probes have been developed that can quickly and conveniently measure these and other parameters without the need for laboratory tests.

In some applications, the sensor probes are removably connected to an upstream probe head, which allows the sensor probes to be easily replaced, repaired, or reconfigured in the field as needed. The probe head receives measurement information from the sensor probe and can communicate the measurement information to an upstream processing device, such as a computer or mobile device. The probe head also supplies power to the removable sensor probe from a power source.

Probes operating in water or other wet environments can experience problems with conductive or galvanic connections between the removable probe and the probe head. Specifically, it has been found that these connection points are susceptible to failure when the pins become bent, broken, corroded, or misaligned. Conductive connectors also require mounting holes in the housing of the probe head and sensor probe, which create potential paths for liquid to enter and damage the probe and/or the probe head. These issues can deteriorate the longevity and reliability of probes that are used to measure parameters of liquid.

SUMMARY

Accordingly, one object of the invention is to provide a probe with improved reliability and longevity by reducing or eliminating failures associated with conductive communication connections between the sensor probe and the probe head.

In one aspect, this disclosure provides a probe that includes (i) a probe head with a first low-power radio frequency (RF) transceiver; and (ii) a sensor probe that is detachably coupled to the probe head and includes a second low-power RF transceiver. The sensor probe can measure a parameter of a liquid while contacting the liquid. The first low-power RF transceiver and the second low-power RF transceiver can form a communication network by which information relating to the measured parameter is transmitted from the second low-power RF transceiver to the first low-power RF transceiver.

In another aspect, this disclosure provides a probe that includes (i) a probe head with a first radio frequency (RF) transceiver and a housing that forms a socket on an exterior surface of the probe head; and (ii) a sensor probe that can measure a parameter of a liquid while contacting the liquid. The sensor probe has a second RF transceiver that transmits information relating to the measured parameter to the first RF transceiver. The sensor probe has a proximal end portion that fits within the socket to detachably couple the sensor probe to the probe head, and when the sensor probe is detachably coupled to the probe head, the socket and the proximal end portion of the sensor probe form an interface that does not include any conductive connections.

DETAILED DESCRIPTION OF EMBODIMENTS

This disclosure describes a probe that is configured to measure one or more parameters of a liquid by submerging the probe in the liquid. The probe includes one or more sensor probes that are detachably coupled to a probe head, which enables the sensor probes to be conveniently replaced or repaired in the field as needed. The sensor probe can measure one or more parameters of the liquid including, for example, pH, conductivity, ORP, dissolved oxygen, turbidity, total suspended solids, carbon dioxide concentration, ozone concentration, chlorine concentration, hydrogen concentration, nitrogen concentration, nitrate concentration, ammonium concentration, etc. The probe can be used to measure a parameter of any liquid including, for example, water, hydrocarbon solvents, oils, oil and gas production fluids, etc. The detachable sensor probes can communicate wirelessly with the probe head using short-range and/or low-power radio transmission. This radio frequency communication, described in greater detail below, enables information to be transmitted between the sensor probe and probe head without using a conductive connection and without requiring holes to be formed in the sensor probe housing and/or probe head housing. Optionally, the probes can include wireless inductive power couplings to transmit power from the probe head to the sensor probe.

Figure 1:
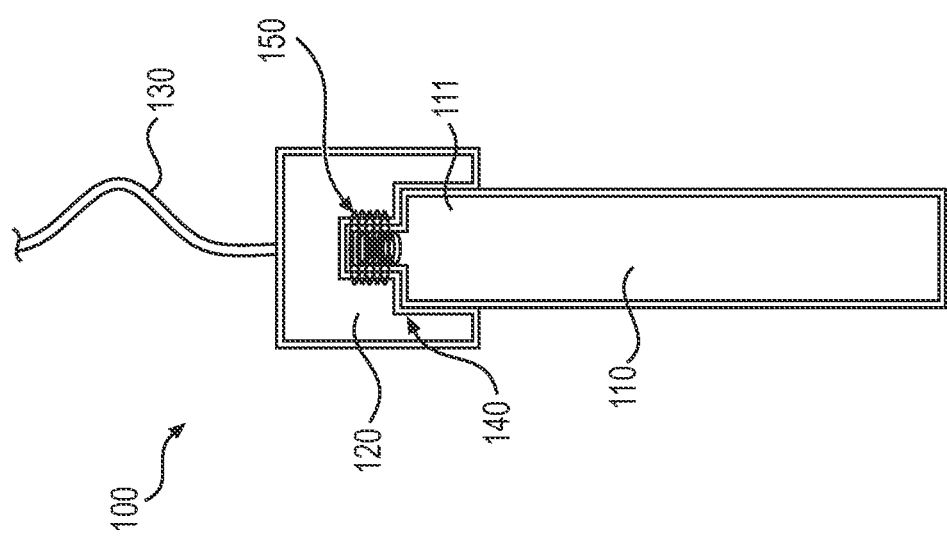
FIG. 1 is a schematic diagram of a probe that is used to measure a liquid parameter according to an embodiment.

FIG. 1 illustrates a probe 100 that includes a sensor probe 110 that is detachably coupled to a probe head 120. The probe head 120 includes socket 140 that is formed on an exterior surface of the housing of the probe head 120, and a proximal end portion 111 of the sensor probe 110 fits within the socket 140 and is surrounded by the socket (i.e., the socket extends 360° around the proximal end portion 111). The sensor probe 110 can be mechanically restrained within the socket 140 by known means, such as corresponding locking structures or other mechanical restraints, magnets, interference fit, etc. The mechanical restraint can be configured so that the sensor probe 110 can be easily removed from the probe head 120, e.g., by hand, to be replaced, repaired, or reconfigured as needed. The probe 100 includes a transmission cable 130 that is connected to an upstream power source (not shown) to transmit power to the probe head 120. The transmission cable 130 can also include wires or optical fibers that can transmit information from the probe head 120 to an upstream processing/controller or logging device that is external to the probe head 120. Likewise, information can be transmitted from the upstream device to the probe 100 such as control signals that can change an operation parameter of the probe 100.

The sensor probe 110 is configured to contact and sense a property of the liquid. The sensor probe 110 can include, for example, a pH sensor probe, a dissolved oxygen sensor probe, a conductivity sensor probe, or an oxidation reduction potential (ORP) probe. The probe 100 can be configured so that the sensor probe 110 and probe head 120 are able to be submerged in the liquid to measure the liquid parameter. As illustrated in connection with FIG. 4 below, the sensor probe 110 communicates with the probe head 120 by using short-range and/or low-power radio frequency signals. Accordingly, the sensor probe 110 can communicate measurement information to the probe head 120 wirelessly without the need for a conductive coupling at the interface between the sensor probe 110 and probe head 120.

FIG. 1 also illustrates an inductive power coupling 150 between the sensor probe 110 and the probe head 120. The inductive power coupling is shown in the embodiments illustrated in FIGS. 1-6. The inductive power coupling is an optional feature of the probes that can enable power to be transmitted from the probe head to the sensor probe(s) without using wires or conductive connections. In alternatives, the power can be transmitted from the probe head to each sensor probe using wires or conductive connections. In other alternatives, the sensor probe can be powered by an internal power source such as a battery, and thus the sensor probe may not receive any power from the probe head. The probes illustrated in FIGS. 2-9 can include similar features as the probe in FIG. 1, or the aforementioned alternatives, with respect to the power transmission and wireless communication.

Figure 2:
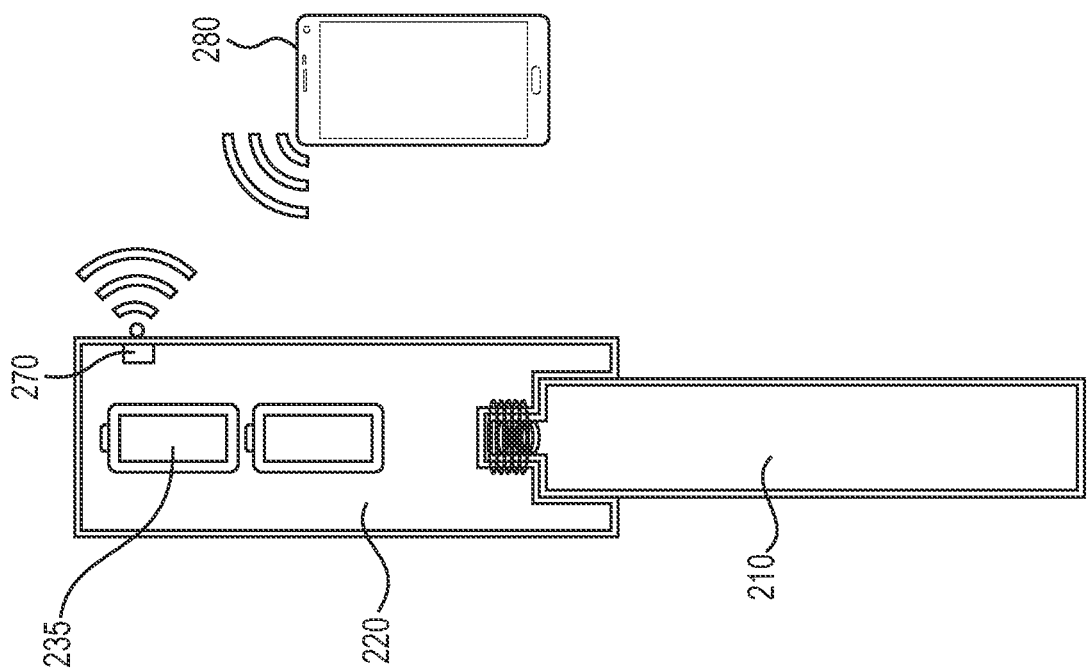
FIG. 2 is a schematic diagram of a probe that is used to measure a liquid parameter according to an embodiment.
Figure 3:
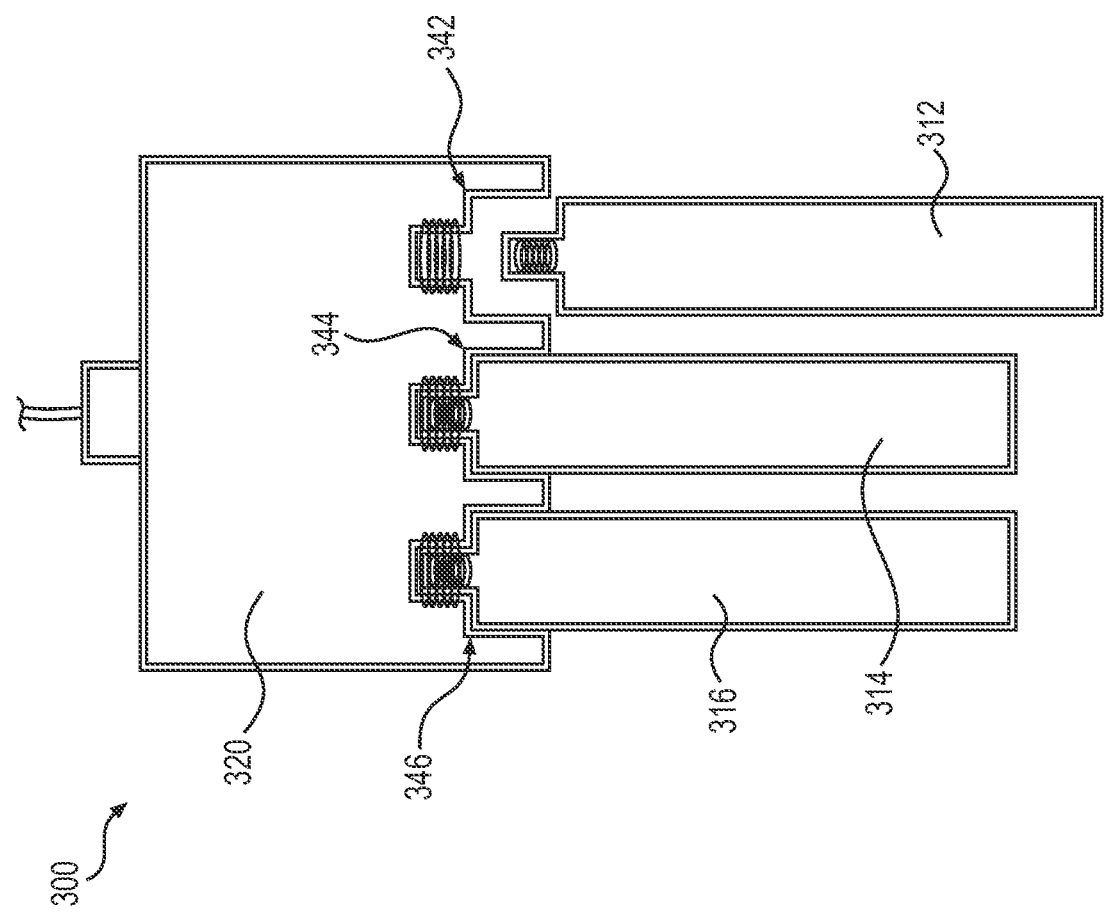
FIG. 3 is a schematic diagram of probe with multiple sensor probes used to measure liquid parameters.

FIG. 2 illustrates an embodiment of a probe 200 that includes a sensor probe 210 that is removably attached to probe head 220. In this embodiment, the probe head 220 includes a battery power source 235 that provides power to operate the sensor probe 210. The probe 200 can communicate wirelessly with an external computing device 280 (e.g., mobile phone) by transmitting information to or from a wireless transceiver 270. This enables information that is measured by the sensor probe 110 to be ultimately transmitted to the computing device 280. The computing device 280 can then further process, analyze, store, and display the information. FIG. 3 illustrates an embodiment of a probe 300 with a multi-sensor probe head that includes three sensor probes 312, 314, 316, each of which measures a different liquid parameter. Similar to the above embodiments, each sensor probe 312, 314, 316 is mechanically restrained in a corresponding socket 342, 344, 346 of the probe head 320 in a detachable manner.

Figure 4:
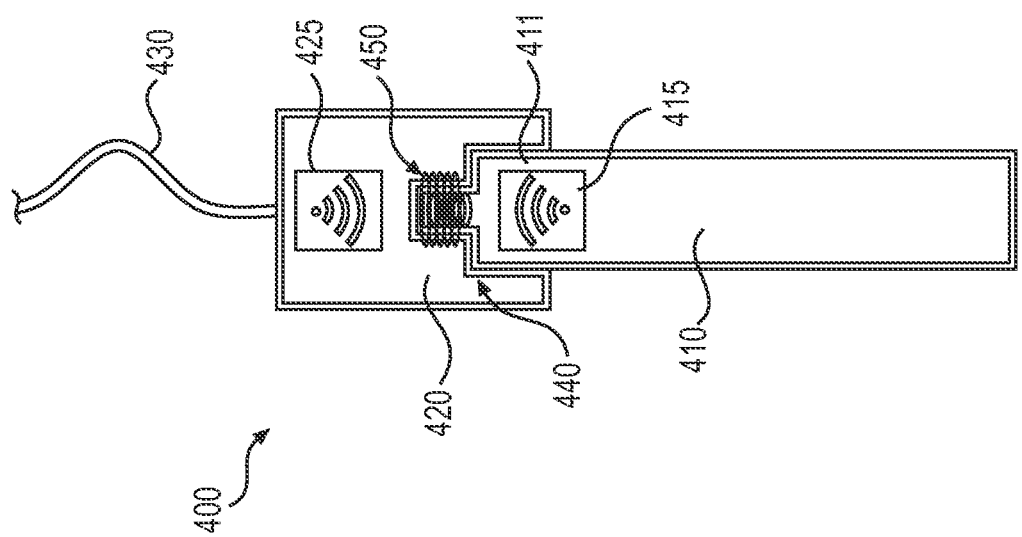
FIG. 4 is a schematic diagram of a probe that is used to measure a liquid parameter according to an embodiment.

FIG. 4 illustrates a probe 400 that includes a sensor probe 410 that is removably attached to the socket 440 of probe head 420. The probe includes a transmission cable 430 that can be connected to an upstream power source (not shown) to transmit power to the probe head. The transmission cable 430 can also include wires or optical fibers that can transmit information from the sensor probe 410 and/or probe head 420 to an upstream device. The probe 400 includes an inductive power coupling 450 between the sensor probe 410 and the probe head 420, which enables power to be transmitted from the probe head to the sensor probe(s) without using wires or conductive connections.

The sensor probe 410 also communicates with the probe head 420 wirelessly to transmit information to the probe head 420. More specifically, FIG. 4 illustrates a first RF transceiver 425 in the probe head 420 and a second RF transceiver 415 in the sensor probe 410 that can form a short-range wireless network to transmit measurement data relating to the measured liquid parameter from the sensor probe 410 to the probe head 420. The term "transceiver" or "RF transceiver" as used herein means a device that can send radio frequency signals, can receive radio frequency signals, or can both send and receive radio frequency signals. The RF transceivers 415, 425 can be low-power radio transceivers that form a data communication channel based on protocols such as Bluetooth, Bluetooth Low Energy (LE), IEEE 802.15.4 (e.g., Zigbee, MiWi, Thread, WirelessHART), Near-field Communication (NFC), and similar. Low-power transceivers can advantageously transmit RF signals over the short distances between the sensor probes and the probe head and can operate at the low power levels that are within the limits of an inductive power coupling. In embodiments, the transceivers can also run for extended periods from a battery power source if needed. The low-power RF transceivers can have a maximum power output that is 80 mW or less, 50 mW or less, from 0.05 mW to 10 mW, from 0.1 mW to 5 mW, or from 0.5 mW to 2.5 mW. Generally, the transceivers on the sensor probe-side (e.g., 415) are powered by power received from the probe head, e.g., through inductive power coupling 450. In some embodiments, for sensor probes with very low power requirements, a passive RF device could be used as the sensor probe-side transceiver to transmit measurement information to the probe head, where the passive RF transceiver is energized by radio waves sent from the probe head-side transceiver.

The RF transceivers can send and/or receive radio transmissions in the ISM band. In embodiments, the transceiver can operate at high frequencies, such as from 1 to 6 GHz, from 2 to 4 GHz, or from 2.2 to 3 GHz. For example, Bluetooth and Bluetooth LE operate at in 2.400-2.4835 GHz spectrum range. Typically, high frequency radio signals become attenuated in liquid such as water, or the liquid otherwise substantially interferes with the signals, which renders the data communication channel unreliable. However, in embodiments, the coupling between the sensor probe and probe head can be arranged to minimize liquid that is present between the transceivers thereby enabling reliable high frequency transmission.

In particular, the socket 440 can be configured to engage closely with the proximate end portion 411 of the sensor probe 410 to inhibit liquid passage between the sensor probe 410 and the probe head 420. As illustrated in FIG. 4, the RF transceiver 415 can also be positioned in the proximate end portion 411 of the sensor probe 410 such that it is at least partially surrounded by socket 440 when the sensor probe 410 is attached to the probe head 420. In embodiments, the sensor probe-side transceiver (e.g., 415) can be arranged to be in the proximal end portion of the sensor probe, e.g., within one fourth of the length of the sensor probe on the side that is proximal to the probe head. Accordingly, during use of the probe 400, the liquid does not interfere with the transmission of information from the sensor probe 410 to the probe head 420 even though the sensor probe and probe head may be submerged in the liquid. Additionally, any liquid that is present between the interface of the sensor probe 410 and the probe head 420 will be displaced when the sensor probe 410 is connected to the socket 440.

The transmission distance between the RF transceiver on the sensor probe-side (e.g., 415) and the RF transceiver on the probe head-side (e.g., 425) can be relatively short. For example, when the sensor probes are attached to the probe head the distance between the RF transceivers can be 0.5 m or less, such as from 0.5 cm to 30 cm, from 1 cm to 10 cm, or from 2 cm to 8 cm, for example. Accordingly, the RF transceivers can be short-range transceivers having a maximum range of 20 m or less, 10 m or less, 1 m or less, or 0.5 m or less.

Figure 8:
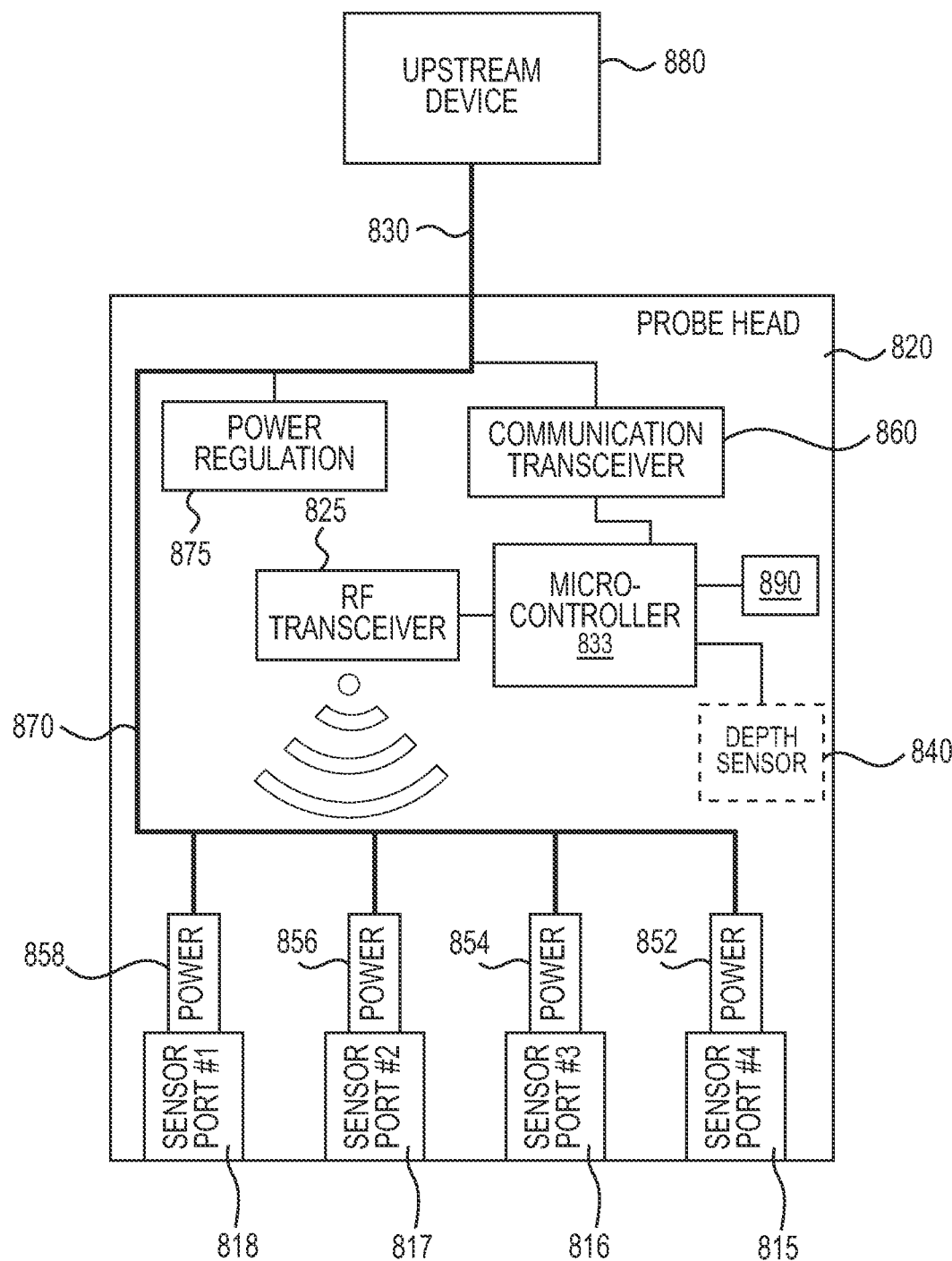
FIG. 8 is a schematic block diagram of a probe head that can be used with multiple sensor probes.

The RF transceivers 415, 425 can establish a data communication network that enables the measurement data collected by the sensor probe to be communicated to the probe head 420. In embodiments, the probe head 420 can also send control signals to the sensor probe 410 to change the operation of the sensor probe 410, to instruct the sensor probe 410 to take a measurement, or to send firmware updates to the sensor probe 410, for example. RF transceiver 415 can form a point-to-point network with transceiver 425. In embodiments where the probe head has multiple sensor probes, such as in FIG. 3, the probe head can include multiple probe head-side transceivers that each form a point-to-point network with a corresponding transceiver on the sensor probe. Alternatively, as illustrated in FIG. 8 below, the probe head can also include a single RF transceiver that forms a star topology network that is able to communicate with each of the transceivers on multiple sensor probes. In other embodiments of probes with multiple sensor probes, the probe head can include one or more transceivers that form a mesh network with the transceivers on the sensor probes. Forming a mesh network would allow the sensor probes to send data to each other, and can extend the range at which the sensors probes can communicate without requiring a high-powered transceiver.

Figure 5:
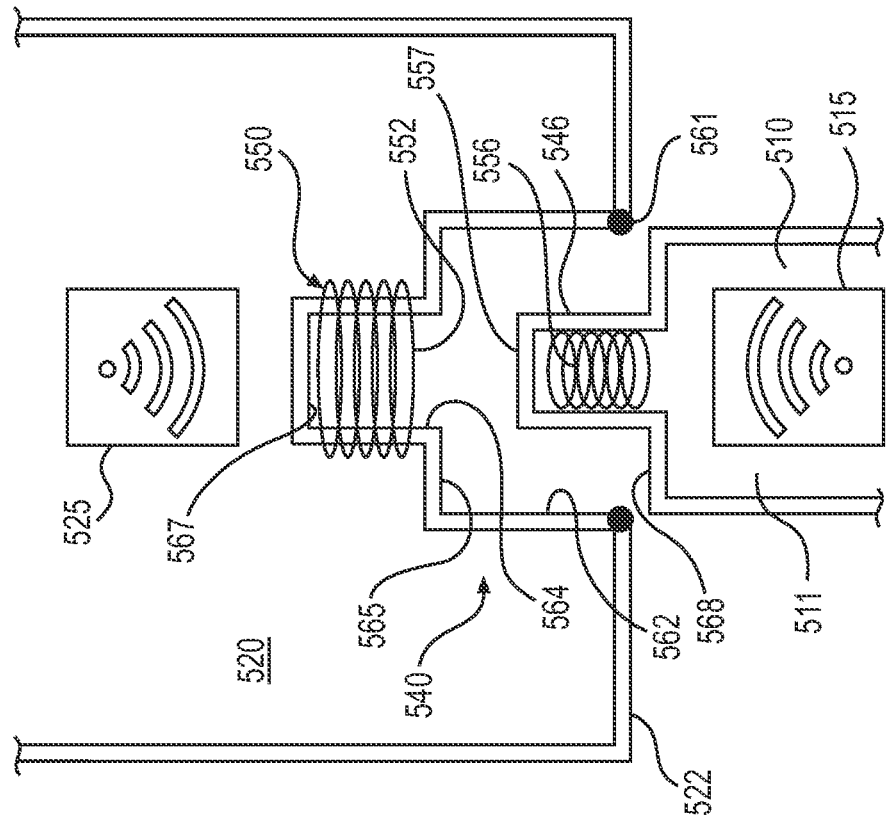
FIG. 5 is a schematic diagram showing an enlarged view of a probe according to an embodiment.

FIG. 5 is an enlarged cross-sectional view of the area near the socket 540 of the probe head 520. The socket 540 is recessed with respect to a distal wall 522 of the probe head housing. In this embodiment, the socket 540 includes a first cylindrical wall 562, a ring-shaped shoulder wall 565, a second cylindrical wall 564, and an end wall 567. The proximal end 511 of the sensor probe 510 includes corresponding walls that can abut and contact the socket walls. For example, the sensor probe 510 can include a protruding portion 546 at the proximal end of the sensor probe 510 that fits within the second cylindrical wall 564 of the socket 540 when the sensor probe 510 is attached to the probe head 520 so that the end wall 557 of the sensor probe 510 contacts and abuts the end wall 567 of the probe head 520. The protruding portion 546 forms a ring-shaped shoulder wall 568 on the sensor probe 510 that abut and contacts shoulder wall 565 of the probe head 520. The socket can optionally include a sealing element 561, such as a rubber O-ring to further prevent or restrict liquid from entering the space between the sensor probe 510 and probe head 520 when submerged during use. As indicated above, the probe head 520 and/or sensor probe 510 can also include mechanical or magnetic fastening elements (not shown) that restrain the sensor probe 510 within the socket 540 in a way that the socket can still be easily detached from the probe head 520.

The sensor probe 510 includes RF transceiver 515 and the probe head includes RF transceiver 525. These can be arranged similarly as described above in connection with FIG. 4 and can use the same protocols to create a short-range wireless network connecting the sensor probe 510 with the probe head 520 so that measurement data detected by sensor probe 510 can be transmitted to the probe head 520.

The probe includes inductive power coupling 550. The inductive power coupling 550 includes a power transmission coil 552 on the probe head 520 and a power reception coil 556 on the sensor probe 510. The inductive coupling includes ferromagnetic material (not pictured) positioned in each of the probe head 520 and sensor probe 510.

The inductive power coupling 550 allows power to be transmitted from the probe head 520 to the sensor probe 510 without any electrical connections or conductive protrusions in the housings of the sensor probe 510 and probe head 520. And since data can also be sent between the sensor probe 510 and the probe head 520 wirelessly, the interface between the probe head 520 and the sensor probe 510, i.e., at least the abutting surfaces of the socket 540 and proximal end portion 511, can be formed without any conductive connections and without any apertures formed in the surfaces of the housings. This can improve reliability and longevity by preventing corrosion and other damage that can cause conductive pins to fail. This arrangement can also improve the longevity and reliability of the probes by preventing any leaks of the liquid into the housing of the sensor probe 510 or the housing of the probe head 520.

Figure 6:
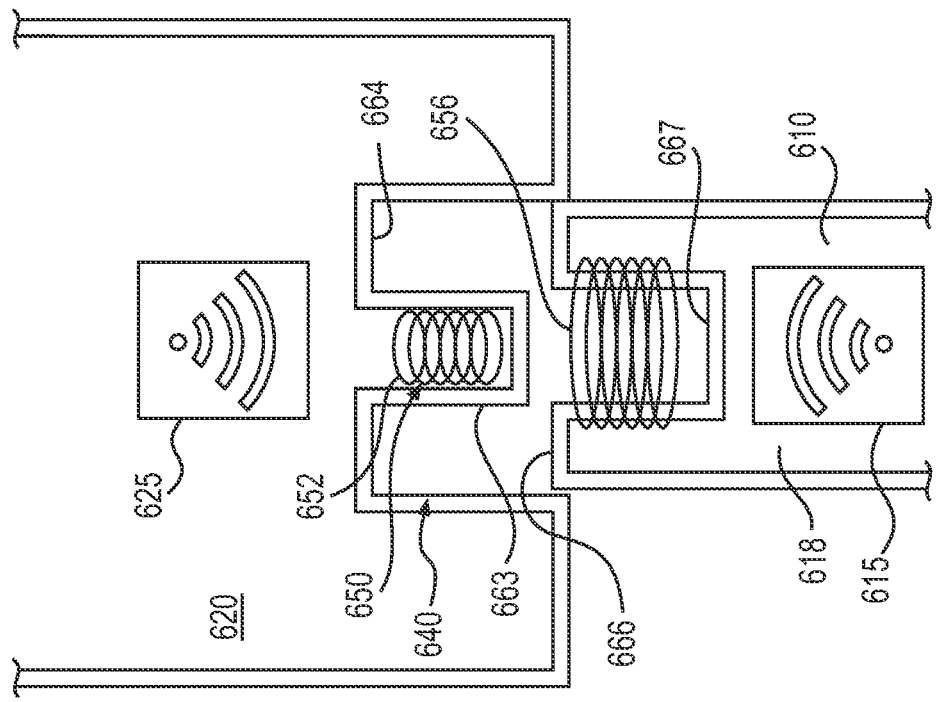
FIG. 6 is a schematic diagram showing an enlarged view of a probe according to an embodiment.

FIG. 6 illustrates a different embodiment of a socket 640 that can be used in connection with this invention. FIG. 6 illustrates a probe head 620 with a socket 640 that is recessed with respect to a distal wall of the probe head housing, but which includes a protruding portion 663 in the center of the socket 640. The sensor probe 610 includes a cylindrically shaped recess 667 that extends into the proximal end portion 618 of the sensor probe 610. The recess 667 surrounds the protruding portion 663 when the sensor probe 610 is attached to the probe head 620. And the proximal end 666 of the sensor probe 610 abuts the end wall 664 of the socket 640 when the sensor probe 610 is attached to probe head 620. The probe includes an inductive power coupling 650 with a power transmission coil 652 on the probe head side and a power reception coil 656 on the sensor probe side.

It should be understood that the socket can have different configurations from the illustrated embodiments. In general, the socket can be configured so that the proximal end of the sensor probe is fit within a recess in the probe head such that the probe head surrounds the end portion. This arrangement helps reduce the amount of liquid that enters the interface between the sensor probe and the probe head when the probe is submerged during use, which allows for reliable RF transmission of the measurement data collected by the sensor probe.

Figure 7:
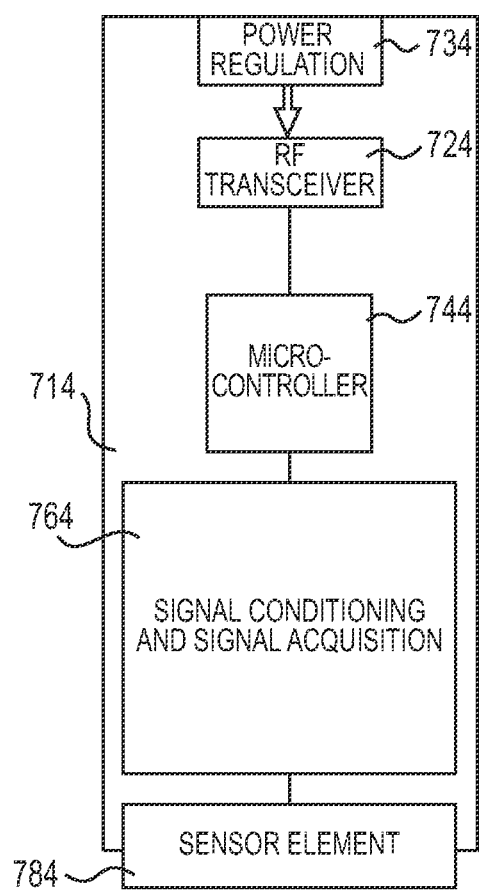
FIG. 7 is a schematic block diagram illustrating a sensor probe that is used to measure one or more liquid parameters.

FIG. 7 is a high-level schematic block diagram that illustrates a sensor probe 714. The sensor probe 714 can represent, for example, a combination pH/ORP sensor probe, a conductivity sensor probe, a luminescent dissolved oxygen (LDO) sensor probe, or a turbidity sensor probe. The sensor probe can be used individually with a corresponding probe head, or one or more of such sensor probes can be used together in a probe with a multi-sensor probe head. FIG. 8 illustrates a multi-sensor probe head that is configured to operate with four of the sensor probes.

The sensor probe 714 includes a power regulation chip 734 that manages the power received from the probe head, e.g., by changing the voltage or by converting the current from AC to DC, for example. The sensor probe 714 includes an RF transceiver 724 that is able to send RF signals to a corresponding RF transceiver in the probe head. The sensor probe 714 includes a microcontroller 744 that controls the operation of the sensor probe, and optionally a memory (not pictured) that can store firmware to operate the sensor probe. The sensor probe 714 includes at least one analog sensing element 784, which can sense a parameter of the liquid while contacting the liquid. The analog sensing element 784 will be different depending on the type of probe. For example, the analog sensing element 784 of a combination pH/ORP sensor probe can sense the pH and ORP of a liquid that is in contact with the analog sensing element. The analog sensing element 784 in a conductivity sensor probe can detect the conductivity of a liquid by passing an electric current through the liquid between electrodes and measuring the conductivity or resistivity of the liquid. The analog sensing element 784 of an LDO probe can include an LED that emits a pulse of blue light onto a luminescent coating, and a photodiode that measures the light emitted from the luminescence coating. The luminescent coating can be positioned in a removable sensor cap. The analog sensing element 784 of a turbidity sensor probe can include an emitter/detector that emits light into a liquid that is in contact with the turbidity sensor probe and measures the amount of light scattered by solids in the liquid.

In some embodiments, the analog sensing element can include a detachable element. For example, an LDO sensor probe can include a detachable sensor cap that includes the luminescent coating. To further reduce the presence of conductive connectors that may be exposed to liquid, in one embodiment, the removable sensor cap or removable sensing element can wirelessly communicate the measurement information to the sensor probe using an RF transceiver. In some embodiments where the power requirements are very low, the removable sensing element can include a passive RF module that is energized by radio waves.

Each sensor probe can also include signal conditioning and signal acquisition circuits 764, which can convert the sensed analog signal to a digital signal. Although not illustrated, the sensor probes 714 can also include a separate temperature sensing element that measures the temperature of the liquid. The sensor probe can compensate or adjust the measured liquid parameter (e.g., pH) based on the temperature of the liquid.

FIG. 8 is a high-level schematic diagram illustrating a probe head 820 that operates with four sensor probes that are detachably coupled to the probe head 820 at sensor port 1 (818), sensor port 2 (817), sensor port 3 (816), and sensor port 4 (815). The probe head 820 is connected to upstream device 880 by a cable 830. The probe head 820 receives power from the upstream device via cable 830 and communicates measurement information to the upstream device 880 via cable 830. The probe head can include a power regulation module 875 that manages the power received from the upstream device 880, e.g., by changing the voltage. Power is distributed to each of the sensor ports by power bus 870. Each sensor port includes an isolated power supply 858, 856, 854, 852, which supplies power to the sensor probes. The isolated power supplies can correspond to the probe head-side inductive power couplings described above. The probe head can include an RF transceiver 825 that is able to network with each of the RF transceivers on the four sensor probes, and can receive RF signals from each of the sensor probes corresponding to measurement information, as described above in connection with FIG. 4. The probe head can include a communications interface 860 that manages communications to and from the upstream device 880.

The probe head 820 can include a memory 890 that enables the probe head to store measurement information received from the sensor probes. The probe head 820 can include a depth sensor 840 that measures the depth in the liquid at which the sensor probes measure the liquid parameters.

Figure 9:
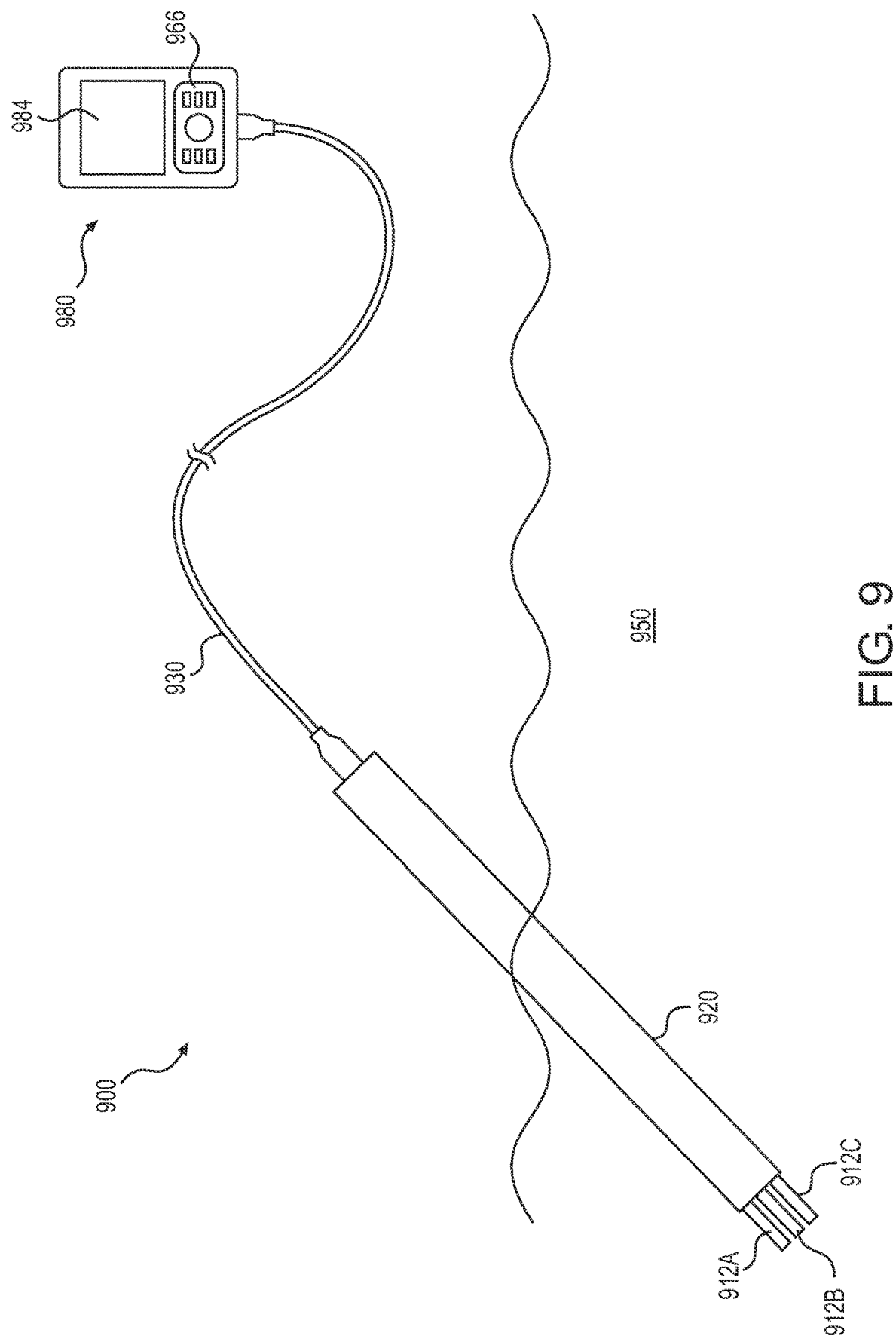
FIG. 9 is a perspective view of a sensor probe that is being used to measure parameters of water.

FIG. 9 illustrates an embodiment of a probe 900 that includes a probe head 920 that includes three sensor probes 912A, 912B, 912C. Each of the sensor probes is detachably coupled to the probe head 920 in the manner described above, and each sensor probe can measure at least one property of water 950. The probe 900 is connected to a hand-held upstream processing device 980 by cable 930.

The upstream processing device 980 includes a user interface 966, a display 984, and a processor (not shown).

In this embodiment, the probe 900 is used as a hand-held field measurement instrument where an operator can continuously measure properties of the water 950 by submerging the probe head 920 and sensor probes 912A, 912B, 912C in the water 950. As can be seen, at least the region of the probe head 920 that includes the socket connections with the sensor probes 912A, 912B, 912C can be fully submerged during use. The operator can view the measurement information on display 984, and can control the display and the operation of the sensor probes through the user interface 966. The arrangements described above enable a wireless communications interface and a wireless power interface between the probe head 920 and the sensor probes 912A, 912B, 912C that is reliable even when submerged in water for extended periods.

In other embodiments, the probes can be configured to be mounted for extended periods (e.g., over several days, several weeks, or more) in a liquid system so that the sensor probe measures the parameters of the liquid over the extended periods. In such cases, the probes can take measurements periodically or at predetermined intervals, and communicate the measurement data to the probe head. The probe head can store or log the measurement data, which can be collected by a user at a later time, and/or the measurement data can be communicated to an external device such as an external computer or other processing system that can store and processes the data.

Although some embodiments of the invention have been described in detail above, those skilled in the art will readily appreciate that many modifications are possible in the example embodiments without materially departing from the disclosed embodiments. Accordingly, all such modifications are intended to be included within the scope of this disclosure as defined in the following claims.

What is claimed is:

1. A probe comprising:
  (i) a probe head that includes a housing that has (a) first low-power radio frequency (RF) transceiver; and (b) a plurality of sockets that are formed on an exterior surface of the probe head; and
  (ii) a plurality of sensor probes that each includes (a) a proximal end portion that fits in a corresponding one of the plurality of sockets to detachably couple the respective sensor probe to the probe head; and (ii) a second low-power RF transceiver, wherein each of the plurality of sensor probes is configured to measure a parameter of a liquid while being detachably coupled to the probe head and while contacting the liquid,
  wherein (i) the first low-power RF transceiver of the probe head and the second low-power RF transceivers of the plurality of sensor probes form a short-range communication network by which information relating to the measured parameter is transmitted from each of the second low-power RF transceivers to the first low-power RF transceiver, (ii) the first low-power RF transceiver is positioned at a distance in a range of from 0.5 cm to 30 cm from each of the second low-power RF transceivers of the plurality of sensor probes, and (iii) the first and second low-power RF transceivers have a maximum power output in a range of from 0.05 mW to 10 mW.

2. The probe of claim 1, wherein when each respective sensor probe of the plurality of sensor probes is detachably coupled to the probe head, the corresponding one of the plurality of sockets surrounds the proximal end portion of the respective sensor probe.

3. The probe of claim 2, wherein each corresponding one of the plurality of sockets is configured to inhibit liquid from entering a space between the probe head and the respective sensor probe when the respective sensor probe is detachably coupled to the probe head.

4. The probe of claim 2, wherein the proximal end portion of the respective sensor probe is mechanically restrained in the corresponding one of the plurality of sockets when the respective sensor probe is detachably coupled to the probe head.

5. The probe of claim 1, wherein the probe head is configured to transmit the information relating to the measured parameter to a processing or logging device that is external to the probe head.

6. The probe of claim 1, wherein the probe further comprises an inductive power coupling that is configured to transmit power from the probe head to the sensor probe.

7. The probe of claim 6, wherein the inductive power coupling comprises a power transmission coil that is located in the probe head, and a power reception coil that is located in the sensor probe.

8. The probe of claim 1, wherein the communication network is based on a protocol selected from one of Bluetooth, Bluetooth Low Energy, IEEE 802.15.4, and Near-field Communication.

9. The probe of claim 1, wherein the first and second low-power RF transceivers have a maximum power output in a range of from 0.1 mW to 5 mW.

10. The probe of claim 1, wherein the first and second low-power RF transceivers operate at frequencies within a range of from 2 GHz to 4 GHz.

11. The probe of claim 1, wherein each of the plurality of sensor probes is configured to measure at least one parameter of the liquid that is selected from pH, conductivity, ORP, dissolved oxygen, turbidity, total suspended solids, carbon dioxide concentration, ozone concentration, chlorine concentration, hydrogen concentration, nitrogen concentration, nitrate concentration, and ammonium concentration.

12. A method of measuring the parameter of the liquid with the probe of claim 1, comprising submerging the probe head and the sensor probe in the liquid and measuring the parameter of the liquid with the sensor probe.

13. The probe of claim 1, wherein each of the plurality of sensor probes is elongate in a first direction and the exterior surface of the probe head extends in a plane that is transverse to the first direction when the sensor probes are detachably coupled to the probe head.

14. The probe of claim 1, wherein each of the plurality of sensor probes is configure to measure a different liquid parameter.

15. The probe of claim 1, wherein the probe head includes a power bus that is configured to distribute power to each of the plurality of sockets to supply power to each of the plurality of sensor probes.

16. The probe of claim 1, wherein the probe head includes from two to four sockets on the exterior surface.

17. The probe of claim 1, wherein the probe is configured to be hand-held by an operator while each of the sensor probes measures the parameter of the liquid, and wherein the probe head is connected by a cable to a hand-held upstream processing device that includes a display.

18. The probe of claim 1, wherein the first low-power RF transceiver is positioned at a distance in a range of from 0.5 cm to 10 cm from each of the second low-power RF transceivers of the plurality of sensor probes.

* * * * *